US008440729B2

(12) United States Patent
Olah et al.

(10) Patent No.: US 8,440,729 B2
(45) Date of Patent: *May 14, 2013

(54) CONVERSION OF CARBON DIOXIDE TO METHANOL USING BI-REFORMING OF METHANE OR NATURAL GAS

(75) Inventors: George A. Olah, Beverly Hills, CA (US); G. K. Surya Prakash, Hacienda Heights, CA (US)

(73) Assignee: University of Southern California, Los Angeles, CA (US)

( * ) Notice: Subject to any disclaimer, the term of this patent is extended or adjusted under 35 U.S.C. 154(b) by 2 days.

This patent is subject to a terminal disclaimer.

(21) Appl. No.: 13/354,042

(22) Filed: Jan. 19, 2012

(65) Prior Publication Data

US 2012/0115965 A1    May 10, 2012

Related U.S. Application Data

(63) Continuation of application No. 12/941,773, filed on Nov. 8, 2010, which is a continuation of application No. 11/850,501, filed on Sep. 5, 2007, now Pat. No. 7,906,559.

(60) Provisional application No. 60/945,501, filed on Jun. 21, 2007.

(51) Int. Cl.
  *C07C 29/151*    (2006.01)
  *C07C 29/157*    (2006.01)
  *B01J 23/847*    (2006.01)

(52) U.S. Cl.
  USPC ........................................................ 518/704

(58) Field of Classification Search .......... None
  See application file for complete search history.

(56) References Cited

U.S. PATENT DOCUMENTS

| 3,993,457 A | 11/1976 | Cahn et al. ............... 48/197 R |
| 4,093,029 A | 6/1978 | Weisz et al. .............. 166/305 R |
| 4,395,495 A | 7/1983 | Cummings ................... 518/704 |
| 4,640,766 A | 2/1987 | Post et al. .................... 208/111 |
| 5,599,638 A | 2/1997 | Surampudi et al. ............ 429/33 |
| 5,767,165 A | 6/1998 | Steinberg et al. ............ 518/703 |
| 7,132,183 B2 | 11/2006 | Galloway ....................... 429/17 |
| 7,605,293 B2 | 10/2009 | Olah et al. .................... 568/885 |
| 7,608,743 B2 | 10/2009 | Olah et al. .................... 568/885 |
| 7,705,059 B2 | 4/2010 | Olah et al. .................... 518/700 |
| 7,795,175 B2 | 9/2010 | Olah et al. .................... 502/401 |
| 2004/0034255 A1 | 2/2004 | Shoji et al. .................... 568/698 |

FOREIGN PATENT DOCUMENTS

| EP | 0 159 759 A2 | 10/1985 |
| GB | 1 545 329 A | 5/1979 |
| WO | WO 2006/113294 A1 | 10/2006 |
| WO | WO 2007/014487 A1 | 2/2007 |

OTHER PUBLICATIONS

International Search Report and Written Opinion of the International Searching Authority, Application No. PCT/US2008/067480, Oct. 1, 2008.
International Search Report, Application No. PCT/US2008/067462, Oct. 1, 2008.
Non-Final Office Action, U.S. Appl. No. 12/941,773, dated Feb. 18, 2011.
Advisory Action Office Action, U.S. Appl. No. 12/941,773, dated Nov. 4, 2011.
Final Office Action, U.S. Appl. No. 12/941,773, dated Jul. 26, 2011.
Non-Final Office Action, U.S. Appl. No. 11/850,501, dated Mar. 19, 2010.
Final Office Action, U.S. Appl. No. 11/850,501, dated Aug. 27, 2010.

*Primary Examiner* — Rosalynd Keys
(74) *Attorney, Agent, or Firm* — Winston & Strawn LLP

(57) ABSTRACT

The invention provides for a method of forming methanol by combining a mixture of methane, water and carbon dioxide under specific reaction conditions sufficient to form a mixture of hydrogen and carbon monoxide which are then reacted under conditions sufficient to form methanol. The molar ratio of hydrogen to carbon monoxide is at least two moles of hydrogen to one mole of carbon monoxide and the overall molar ratio between methane, water and carbon dioxide is about 3:2:1. Methane, carbon dioxide and water are bi-reformed over a catalyst. The catalyst includes a single metal, a metal oxide, a mixed catalyst of a metal and a metal oxide or a mixed catalyst of at least two metal oxides.

20 Claims, 1 Drawing Sheet

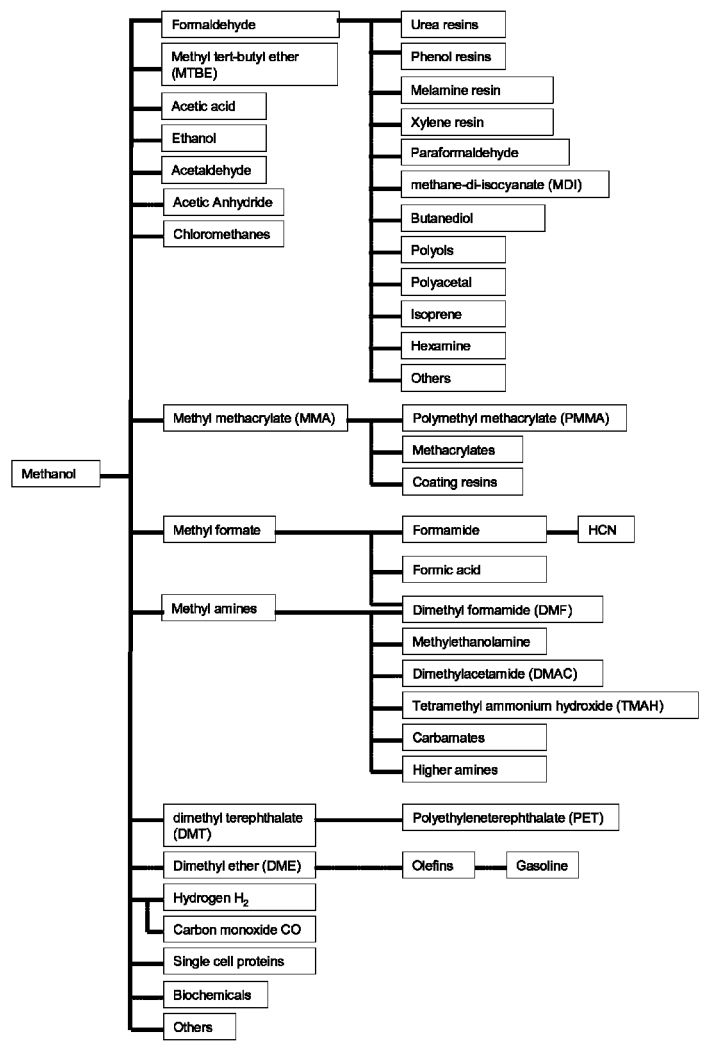
PRIOR ART

CONVERSION OF CARBON DIOXIDE TO METHANOL USING BI-REFORMING OF METHANE OR NATURAL GAS

CROSS-REFERENCE TO RELATED APPLICATIONS

This application is a continuation of application Ser. No. 12/941,773 filed Nov. 8, 2010, which is a continuation of application Ser. No. 11/850,501 filed Sep. 5, 2007, now U.S. Pat. No. 7,906,559, which claims the benefit of application No. 60/945,501 filed Jun. 21, 2007. Each document is expressly incorporated herein by reference thereto.

BACKGROUND

Hydrocarbons are essential in modern life. Hydrocarbons are used as fuel and raw material in various fields, including the chemical, petrochemical, plastics, and rubber industries. Fossil fuels, such as coal, oil and natural gas, are composed of hydrocarbons with varying ratios of carbon to hydrogen. Despite their wide application and high demand, fossil fuels also have limitations and disadvantages, particularly due to their finite reserve, irreversible combustion and contribution to air pollution (and thus to global warming). Regardless of these problems the more efficient use of still existing natural gas sources is highly desirable. Further new sources and ways for recyclable and environmentally benign carbon fuels are needed.

One alternative frequently mentioned non-carbon fuel is hydrogen, and its use in the so-called "hydrogen economy." Hydrogen is thought to be beneficial as a clean fuel, producing only water when combusted. Free hydrogen, however, is not a natural primary energy source on earth, due to its incompatibility with the atmospheric oxygen. It must be generated from hydrocarbons or water, which is a highly energy-consuming process. Further, as hydrogen is produced from hydrocarbons or coal, any claimed benefit of hydrogen as a clean fuel is outweighed by the fact that its generation, mainly by reforming of natural gas, oil or coal to synthesis gas ("syn-gas" a mixture of CO and $H_2$), or the generation of electricity for the electrolysis of water is far from clean, besides hydrogen is difficult and costly to handle, transport and distribute. As it is extremely light, volatile and potentially explosive, it requires high-pressure equipment. The needed non-existent infrastructure also necessitates special materials to minimize diffusion and leakage, and extensive safety precautions to prevent explosions.

The continued importation of natural gas from far away and frequently difficult to access locations also necessitates its safe storage and transportation particularly when involving liquefied natural gas (LNG). This necessitates transporting LNG at low temperatures in its liquid form exposing it to serious environmental and safety hazards. It is suggested that a more practical and safe alternative for LNG is methanol, or dimethyl ether (DME), which are readily produced from natural gas. Methanol is the simplest liquid oxygenated hydrocarbon, differing from methane ($CH_4$) by a single additional oxygen atom. Methanol, also called methyl alcohol or wood alcohol, is a colorless, water-soluble liquid with a mild alcoholic odor. It is easy to store and transport. It freezes at −97.6° C., boils at 64.6° C., and has a density of 0.791 at 20° C.

Methanol is a convenient safe liquid easily obtained from existing coal or natural gas sources via methods developed and practiced since the 1920's. However, these methods using conversion (reforming) of coal and subsequently natural gas to syn-gas (a mixture of $H_2$ and CO) are highly energy consuming and produce large amount of $CO_2$ as a by-product. This is notably an economic disadvantage but also represents a serious environmental problem by increasing one of the main greenhouse gas causing global warming.

Methanol not only represent a convenient and safe way to store and transport energy, but together with its derived product dimethyl ether (DME), is an excellent fuel. Dimethyl ether is easily obtained from methanol by dehydration or from methane (natural gas) with $CO_2$ via a bi-reforming process. It is a particularly effective fuel for diesel engines because of its high cetane number and favorable combustion properties. Methanol and dimethyl ether exceedingly blend well with gasoline or diesel oil to be used as fuels in internal combustion engines or electricity generators. One of the most efficient use of methanol is in fuel cells, particularly in direct methanol fuel cells (DMFC), in which methanol is directly oxidized with air to carbon dioxide and water while producing electricity.

Contrary to gasoline, which is a complex mixture of many different hydrocarbons and additives, methanol is a single simple chemical compound. It contains about half the energy density of gasoline, meaning that two liters of methanol provide the same energy as a liter of gasoline. Even though the energy content of methanol is lower, it has a higher octane rating of 100 (average of the research octane number (RON) of 107 and motor octane number (MON) of 92), which means that the fuel/air mixture can be compressed to a smaller volume before being ignited. This allows the engine to run at a higher compression ratio of 10-11 to 1 more efficiently than the 8-9 to 1 ratio of a gasoline-powered engine. Efficiency is also increased by methanol's (oxygenates') higher "flame speed," which enables faster, more complete fuel combustion in the engines. These factors explain the high efficiency of methanol despite its lower energy density than gasoline. Further, to render methanol more ignitable even under the most frigid conditions, methanol is mixed with gasoline, and other volatile components or with a device to vaporize or atomize methanol. For example, an effective automotive fuel comprised by adding methanol to gasoline with the fuel having a minimum gasoline content of at least 15% by volume (M85 fuel) so that the engine can readily start even in low temperature environments were commercially used in the US in the 1980's. M20fuel (with 20 volume % methanol) is also being introduced. Similarly, dimethyl ether (DME) mixed with diesel oil or in household use as a substitute of natural gas or LPG is of commercial interest. These mixtures are not only efficient fuels but conserve or replace decreasing oil resources. The amount of methanol or dimethyl ether added can be determined depending upon the specific condition and needs.

Methanol has a latent heat of vaporization of about 3.7 times higher than gasoline, and can absorb a significantly larger amount of heat when passing from liquid to gaseous state. This helps to remove heat away from the engine and enables the use of an air-cooled radiator instead of a heavier water-cooled system. Thus, compared to a gasoline-powered car, a methanol-powered engine provides a smaller, lighter engine block, reduced cooling requirements, and better acceleration and mileage capabilities. Methanol and DME are also more environmentally-friendly than gasoline or diesel oil, and produce low overall emissions of air pollutants such as certain hydrocarbons, $NO_x$, $SO_2$ and particulates.

Methanol is also one of the safest fuels available. Compared to gasoline, its physical and chemical properties significantly reduce the risk of fire. Methanol has lower volatility, and methanol vapor must be four times more concentrated than gasoline for ignition to occur. Even when ignited, methanol burns about four times slower than gasoline, releases heat only at one-eighth the rate of gasoline fire, and is far less likely to spread to surrounding ignitable materials because of the low radiant heat output. It has been estimated by the EPA that switching from gasoline to methanol would reduce incidence of fuel-related fire by 90%. Methanol burns with a colorless flame, but additives can solve this problem. As methanol is completely miscible with water not only it is environmentally readily decomposed in nature but in contrast to ethanol there are no strict requirements needed to keep it dry to avoid phase separation from gasoline.

Methanol also provides an attractive and more environmentally-friendly alternative to diesel fuel. It does not produce smoke, soot, or particulates when combusted, in contrast to diesel fuel, which generally produces polluting particles during combustion. It also produce very low emissions of NO because it burns at a lower temperature than diesel. Furthermore, it has a significantly higher vapor pressure compared to diesel fuel, and the higher volatility allows easy start even in cold weather, without producing smoke typical of cold start with a conventional diesel engine. If desired, additives or ignition improvers, such as octyl nitrate, tetrahydrofurfuryl nitrate, peroxides or higher alkyl ethers, can be added to bring methanol's cetane rating to the level closer to diesel. Methanol is also used in the manufacture of biodiesel fuels by esterification of fatty acids.

As mentioned, the closely related derivative of methanol, which is a highly desirable alternative fuel, is dimethyl ether. Dimethyl ether ($CH_3OCH_3$), the simplest of all ethers, is a colorless, nontoxic, non-corrosive, non-carcinogenic and environmentally friendly chemical that is mainly used today as an aerosol propellant in spray cans, in place of the banned CFC gases. Dimethyl ether has a boiling point of −25° C., and is a gas under ambient conditions. Dimethyl ether is, however, easily handled as a liquid and stored in pressurized tanks, much like liquefied petroleum gas (LPG). The interest in dimethyl ether as alternative fuel lies in its high cetane rating of 55 to 60, which is much higher than that of methanol and is also higher than the cetane rating of 40 to 55 of conventional diesel fuels. The cetane rating indicates that dimethyl ether is effectively used in diesel engines. Advantageously, dimethyl ether, like methanol, is clean burning, and produces no soot particulates, black smoke or $SO_2$, and only very low amounts of $NO_x$ and other emissions even without after-treatment of its exhaust gas. Some of the physical and chemical properties of DME, in comparison to diesel fuel, are shown in Table 1.

TABLE 1

Comparison of the physical properties of DME and diesel fuel

| | Dimethyl Ether | Diesel Fuel |
|---|---|---|
| Boiling point ° C. | −24.9 | 180-360 |
| Vapor pressure at 20° C. (bar) | 5.1 | — |
| Liquid density at 20° C. (kg/m) | 668 | 840-890 |
| Heating value (kcal/kg) | 6,880 | 10,150 |
| Cetane number | 55-60 | 40-55 |
| Autoignition temperature (° C.) | 235 | 200-300 |
| Flammability limits in air (vol %) | 3-17 | 0.6-6.5 |

Currently, dimethyl ether is produced by the direct dehydration of methanol according to the following reaction:

$$2CH_3OH \rightarrow CH_3OCH_3 + H_2O$$

Another methanol derivative is dimethyl carbonate (DMC), which can be obtained by converting methanol with phosgene or by oxidative carbonylation of methanol. DMC has a high cetane rating, and can be blended into diesel fuel in a concentration up to 10%, reducing fuel viscosity and improving emissions.

Methanol and its derivatives, e.g., dimethyl ether, DMC, and biodiesel fuel (esters of naturally occurring unsaturated acids) already have significant and expanding uses. They can be used, for example, as a substitute for gasoline and diesel fuel in ICE-powered cars with only minor modifications to the existing engines and fuel systems. Methanol can also be used in fuel cells, for fuel cell vehicles (FCVs), which are considered to be the best alternatives to ICEs in the transportation field. DME is also starting to be used in admixture to LNG and LPG in domestic and industrial fuel uses.

Methanol can also be used in reforming to produce hydrogen. In an effort to address the problems associated with hydrogen storage and distribution, suggestions have been made to use liquids rich in hydrogen such as gasoline or methanol as a source of hydrogen in vehicles via an on-board reformer. It was emphasized that methanol is the safest of all materials available for such hydrogen production. Further, because of the high hydrogen content of liquid methanol, even compared to pure cryogenic hydrogen (98.8 g of hydrogen in a liter of methanol at room temperature compared to 70.8 g in liquid hydrogen at about −253° C.), methanol is an excellent carrier of hydrogen fuel. The absence of C—C bonds in methanol, which are more difficult to break, facilitates its transformation to pure hydrogen in 80 to 90% efficiency.

In contrast to a pure hydrogen-based storage system, a reformer system is compact, containing on a volume basis more hydrogen than even liquid hydrogen, and is easy to store and handle without pressurization. A methanol steam reformer is also advantageous in allowing operation at a much lower temperature (250° C. to 350° C.) and for being better adapted to on-board applications. Furthermore, methanol contains no sulfur, a contaminant for fuel cells, and no nitrogen oxides are formed from a methanol reformer because of the lower operating temperature. Particulate matter and $NO_x$ emissions are virtually eliminated, and other emissions are minimal. Moreover, methanol allows refueling to be as quick and easy as with gasoline or diesel fuel. Thus, an on-board methanol reformer enables rapid and efficient delivery of hydrogen from liquid fuel that can be easily distributed and stored in the vehicle. To date, methanol is the only liquid fuel that has been demonstrated on a practical scale to be a suitable liquid fuel for a reformer to produce hydrogen for use in a fuel cells for transportation applications.

In addition to on-board reforming, methanol also enables convenient production of hydrogen in fueling stations for refueling hydrogen fuel cell vehicles. A fuel cell, an electrochemical device that converts free chemical energy of fuel directly into electrical energy, provides a highly efficient way of producing electricity via catalytic electrochemical oxidation. For example, hydrogen and oxygen (air) are combined in an electrochemical cell-like device to produce water and electricity. The process is clean, with water being the only byproduct. However, because hydrogen itself must first be produced in an energy-consuming process, by electrolysis or from a hydrocarbon source (fossil fuel) with a reformer, hydrogen fuel cells are still necessarily limited in their utility.

A system for producing high purity hydrogen has been developed by steam reforming of methanol with a highly active catalyst, which allows operation at a relatively low temperature (240° C. to 290° C.) and enables flexibility in operation as well as rapid start-up and stop. These methanol-to-hydrogen (MTH) units, ranging in production capacity from 50 to 4000 m³ $H_2$ per hour, are already used in various industries, including the electronic, glass, ceramic, and food processing industries, and provide excellent reliability, prolonged life span, and minimal maintenance. As described above, operating at a relatively low temperature, the MTH process has a clear advantage over reforming of natural gas and other hydrocarbons which must be conducted at above 600° C., because less energy is needed to heat methanol to the appropriate reaction temperature.

The usefulness of methanol has led to the development of other reforming processes, for example, a process known as oxidative steam reforming, which combines steam reforming, partial oxidation of methanol, using novel catalyst systems. Oxidative steam reforming produces high purity hydrogen with zero or trace amounts of CO, at high methanol conversion and temperatures as low as 230° C. It has the advantage of being, contrary to steam reforming, an exothermic reaction, therefore, minimizing energy consumption. There is also auto thermal reforming of methanol, which combines steam reforming and partial oxidation of methanol in a specific ratio and addresses any drawback of an exothermic reaction by producing only enough energy to sustain itself. Auto thermal reforming is neither exothermic nor endothermic, and does not require any external heating once the reaction temperature is reached. Despite the aforementioned possibilities, hydrogen fuel cells must use highly volatile and flammable hydrogen or reformer systems.

U.S. Pat. No. 5,599,638 discloses a simple direct methanol fuel cell (DMFC) to address the disadvantages of hydrogen fuel cells. In contrast to a hydrogen fuel cell, the DMFC is not dependent on generation of hydrogen by processes such as electrolysis of water or reformation of natural gas or hydrocarbons. The DMFC is also more cost effective because methanol, as a liquid fuel, does not require cooling at ambient temperatures or costly high pressure infrastructure and can be used with existing storage and dispensing units, unlike hydrogen fuel, whose storage and distribution requires new infrastructure. Further, methanol has a relatively high theoretical volumetric energy density compared to other systems such as conventional batteries and the $H_2$-PEM (PEM: proton exchange membrane) fuel cell. This is of great importance for small portable applications (cellular phones, laptop computers, etc.), for which small size and weight of energy unit is desired.

DMFC offers numerous benefits in various areas, including the transportation sector. By eliminating the need for a methanol steam reformer, DMFC significantly reduces the cost, complexity and weight of the vehicle, and improves fuel economy. A DMFC system is also comparable in its simplicity to a direct hydrogen fuel cell, without the cumbersome problems of on-board hydrogen storage or hydrogen producing reformers. Because only water and $CO_2$ are emitted, emissions of other pollutants (e.g., $NO_x$, particulate matter, $SO_2$, etc.) are eliminated. Direct methanol fuel cell vehicles are expected to be of low emission (ZEV), and use of methanol fuel cell vehicles will greatly eliminate air pollutants from vehicles in the long term. Further, unlike internal combustion engine vehicles, the emission profile is expected to remain nearly unchanged over time. New fuel cell membranes based on hydrocarbon or hydrofluorocarbon materials with reduced cost and crossover characteristics have been developed that allow room temperature efficiency of about 34%.

Methanol and dimethyl ether provide a number of important advantages as transportation fuels. By contrast to hydrogen, methanol storage does not require any energy intensive procedures for pressurization or liquefaction. Because it is a liquid at room temperature, it can be easily handled, stored, distributed and carried in vehicles. It can act as an ideal hydrogen carrier for fuel cell vehicles through on-board methanol reformers or can be used directly in DMFC vehicles. Dimethyl ether although gaseous at room temperature can be easily stored under modest pressure and used effectively in admixture with diesel fuels and liquefied natural gas (LNG), or used in residential gas mixtures.

Methanol is also an attractive liquid fuel for static applications. For example, methanol can be used directly as fuel in gas turbines to generate electric power. Gas turbines typically use natural gas or light petroleum distillate fractions as fuel. Compared to such fuels, methanol can achieve higher power output and lower $NO_x$ emissions because of its lower flame temperature. Since methanol does not contain sulfur, $SO_2$ emissions are also eliminated. Operation on methanol offers the same flexibility as on natural gas and distillate fuels, and can be performed with existing turbines, originally designed for natural gas or other fossil fuels, after relatively easy modification. Methanol is also an attractive fuel since fuel-grade methanol, with lower production cost than higher purity chemical-grade methanol, can be used in turbines. Because the size and weight of a fuel cell is of less importance in static applications than mobile applications, various fuel cells other than PEM fuel cells and DMFC, such as phosphoric acid, molten carbonate and solid oxide fuel cells (PAFC, MCFC, and SOFC, respectively), can also be used.

In addition to use as fuels, methanol, dimethyl ether and derived chemicals have significant applications in the chemical industry. Today, methanol is one of the most important feedstock in the chemical industry. The majority of the some 35 million tons of the annually produced methanol are used to manufacture a large variety of chemical products and materials, including basic chemicals such as formaldehyde, acetic acid, MTBE (although it is increasingly phased out for environmental reasons), as well as various polymers, paints, adhesives, construction materials, and others. Worldwide, methanol is used to produce formaldehyde (38%), methyl-tert-butyl ether (MTBE, 20%) and acetic acid (11%). Methanol is also a feedstock for chloromethanes, methylamines, methyl methacrylate, and dimethyl terephthalate, among others. These chemical intermediates are then processed to manufacture products such as paints, resins, adhesives, antifreeze, and plastics. Formaldehyde, produced in large quantities from methanol, is mainly used to prepare phenol-, urea- and melamine-formaldehyde and polyacetal resins as well as butanediol and methylene bis(4-phenyl isocyanate) MDI foam, which is used as insulation in refrigerators, doors, and in car dashboards and bumpers. Formaldehyde resins are predominantly used as adhesives in a wide variety of applications, e.g., manufacture of particle boards, plywood and other wood panels. Examples of major methanol-derived chemical products and materials produced are listed in FIG. 1.

In producing basic chemicals, raw material feedstock constitutes typically up to 60-70% of the manufacturing costs. The cost of feedstock therefore plays a significant economic role and its continued availability is essential. Because of its economic and long range availability advantages, methanol is considered a potential prime feedstock for processes currently utilizing more expensive feedstock such as ethylene and propylene, to produce chemicals including acetic acid, acetaldehyde, ethanol, ethylene glycol, styrene, and ethylbenzene, and various synthetic hydrocarbon products. For example, direct conversion of methanol to ethanol can be achieved using a rhodium-based catalyst, which has been found to promote the reductive carbonylation of methanol to acetaldehyde with selectivity close to 90%, and a ruthenium catalyst, which further reduces acetaldehyde to ethanol.

Another feasible way to produce ethanol from methanol involves conversion of ethylene follow by hydration according to the overall reaction:

$$2CH_3OH \rightarrow C_2H_5OH + H_2O$$

Producing ethylene glycol via methanol oxidative coupling instead of using ethylene as feedstock is also pursued, and significant advances for synthesizing ethylene glycol from dimethyl ether, obtained by methanol dehydration, have also been made.

Conversion of methanol to olefins such as ethylene and propylene, also known as methanol to olefin (MTO) technology, is particularly promising considering the high demand for olefins, especially in polyolefin and synthetic hydrocarbon products production. The MTO technology is presently a two-step process, in which natural gas is converted to methanol via syn-gas and methanol is then transformed to olefin. It is considered that in the process, methanol is first dehydrated to dimethyl ether (DME), which then reacts to form ethylene and/or propylene. Small amounts of butenes, higher olefins, alkanes, and aromatics are also formed.

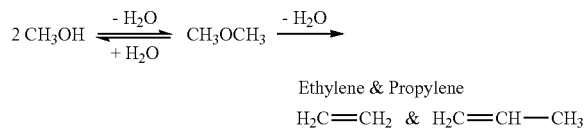

Various catalysts, include without limitation, synthetic aluminosilicate zeolite catalysts, such as ZSM-5 (a zeolite developed by Mobil), silicoaluminophosphate (SAPO) molecular sieves such as SAPO34 and SAPO-17 (UOP), as well as bi-functional supported acid-base catalysts such as tungsten oxide over alumina $WO_3/Al_2O_3$, have been found to be active in converting methanol to ethylene and propylene at a temperature between 250° C. and 400° C. The nature and amount of the end product depend on the type of the catalyst, contact time and other factors of the process used. Depending on the operating conditions, the weight ratio of propylene to ethylene can be modified between about 0.77 and 1.33, allowing considerable flexibility. For example, when using SAPO-34 catalyst according to an MTO process developed by UOP and Norsk Hydro, methanol is converted to ethylene and propylene at more than 80% selectivity, and also to butene, a valuable starting material for a number of products, at about 10%. When using an MTO process developed by Lurgi with ZSM-5 catalysts, mostly propylene is produced at yields above 70%. A process developed by ExxonMobil, with ZSM-5 catalyst, produces hydrocarbons in the gasoline and/or distillate range at selectivity greater than 95%.

There is also a methanol to gasoline (MTG) process, in which medium-pore zeolites with considerable acidity, e.g., ZSM-5, are used as catalysts. In this process, methanol is first dehydrated to an equilibrium mixture of dimethyl ether, methanol and water over a catalyst, and this mixture is then converted to light olefins, primarily ethylene and propylene. The light olefins can undergo further transformations to higher olefins, $C_3$-$C_6$ alkanes, and $C_6$-$C_{10}$ aromatics such as toluene, xylenes, and trimethylbenzene.

With decreasing oil and natural gas reserves, it is inevitable that synthetic hydrocarbons would play a major role. Thus, methanol-based synthetic hydrocarbons and chemicals available through MTG and MTO processes are assuming increasing importance in replacing oil and gas-based materials. The listed uses of methanol in FIG. 1 are only illustrative and not limiting.

Methanol can also be used as a source of single cell proteins. A single cell protein (SCP) refers to a protein produced by a microorganism which degrades hydrocarbon substrates while gaining energy. The protein content depends on the type of microorganism, e.g., bacteria, yeast, mold, etc. The SCP has many uses, including uses as food and animal feed.

Considering the numerous uses of methanol and dimethyl ether, it is clearly desirable to have improved and efficient methods for their production. Currently, methanol is almost exclusively made from synthesis gas obtained from incomplete combustion (or catalytic reforming) of fossil fuel, mainly natural gas (methane) and coal.

Methanol can also be made from renewable biomass, but such methanol production also involves syn-gas and may not be energetically favorable and limited in terms of scale. As used herein, the term "biomass" includes any type of plant or animal material, i.e., materials produced by a life form, including wood and wood waste, agricultural crops and their waste byproducts, municipal solid waste, animal waste, aquatic plants, and algae. The method of transforming biomass to methanol is similar to the method of producing methanol from coal, and requires gasification of biomass to syn-gas, followed by methanol synthesis by the same processes used with fossil fuel. Use of biomass also presents other disadvantages, such as low energy density and high cost of collecting and transporting bulky biomass. Although recent improvements involving the use of "biocrude," black liquid obtained from fast pyrolysis of biomass, is somewhat promising, more development is needed for commercial application of biocrude.

The presently existing methods of producing methanol involve syn-gas. Syn-gas is a mixture of hydrogen, carbon monoxide and carbon dioxide, and produces methanol over a heterogeneous catalyst according to the following reactions:

$$CO + 2H_2 \rightarrow CH_3OH \quad \Delta H_{298K} = -21.7 \text{ kcal/mol}$$

$$CO_2 + 3H_2 \rightarrow CH_3OH + H_2O \quad \Delta H_{298K} = -9.8 \text{ kcal/mol}$$

$$CO_2 + H_2 \rightarrow CO + H_2O \quad \Delta H_{298K} = 11.9 \text{ kcal/mol}$$

The first two reactions are exothermic with heat of reaction equal to about 21.7 kcal·mol/l and about 9.8 kcal·mol/l, respectively, and result in a decrease in volume. Conversion to methanol is favored by increasing the pressure and decreasing the temperature according to Le Chatelier's principle. The third equation describes the endothermic reverse water gas shift reaction (RWGSR). Carbon monoxide produced in the third reaction can further react with hydrogen to produce methanol. The second reaction is simply the sum of the first and the third reactions. Each of these reactions is reversible, and is therefore limited by thermodynamic equilibrium under the reaction conditions, e.g., temperature, pressure and composition of the syn-gas.

Synthesis gas for methanol production can be obtained by reforming or partial oxidation of any carbonaceous material, such as coal, coke, natural gas, petroleum, heavy oil, and asphalt. The composition of syn-gas is generally characterized by the stoichiometric number S, corresponding to the reaction shown below.

$$S = \frac{(\text{moles } H_2 - \text{moles } CO_2)}{(\text{moles } CO + \text{moles } CO_2)}$$

Ideally, S should be equal to or slightly above 2. A value above 2 indicates excess hydrogen, while a value below 2 indicates relative hydrogen deficiency. Reforming of feedstock having a higher H/C ratio, such as propane, butane or naphthas, leads to S values in the vicinity of 2, ideal for the conversion to methanol. When coal is used, however, additional treatment is required to obtain an optimal S value. Synthesis gas from coal requires treatment to avoid formation of undesired byproducts.

The most widely used technology to produce syn-gas for methanol synthesis is steam reforming. In this process, natural gas (of which methane is the major component) is reacted in a highly endothermic reaction with steam over a catalyst, typically based on nickel, at a temperature of about 800° C. to about 1,000° C., and a pressure of about 20 atm to 30 atm) to form CO and $H_2$. A part of the CO formed reacts consequently with steam in the water gas shift reaction (WGS) to yield more $H_2$ and also $CO_2$. The gas obtained is thus a mixture of $H_2$, CO and $CO_2$ in various concentrations depending on the reaction conditions, such as temperature, pressure and $H_2O$/$CH_4$ ratio according to the following reactions:

$$CH_4 + H_2O \rightarrow CO + 3H_2 \; \Delta H_{298K} = 49.1 \text{ kcal/mol}$$

$$CO + H_2O \rightarrow CO_2 + H_2 \; \Delta H_{298K} = -9.8 \text{ kcal/mol}$$

Since the overall methane steam reforming process is highly endothermic, heat must be supplied to the system by burning a part of the natural gas used as the feedstock. The stoichiometric number S obtained by steam reforming of methane is close to 3, much higher than the desired value of 2. This can generally be corrected by addition of $CO_2$ to the steam reformer's exit gas or use of excess hydrogen in some other process such as ammonia synthesis. However, natural gas is still the preferred feedstock for methanol production because it offers high hydrogen content and, additionally, the lowest energy consumption, capital investment and operating costs. Natural gas also contains fewer impurities such as sulfur, halogenated compounds, and metals which may poison the catalysts used in the process.

The existing processes invariably employ extremely active and selective copper-based catalysts, differing only in the reactor design and catalyst arrangement. Because only part of the syn-gas is converted to methanol after passing over the catalyst, the remaining syn-gas is recycled after separation of methanol and water. There is also a more recently developed liquid phase process for methanol production, during which the syn-gas is bubbled into the reaction mixture. Although the existing processes have methanol selectivity greater than 99% and energy efficiency above 70%, crude methanol leaving the reactor still contains water and other impurities, such as dissolved gases (e.g., methane, CO, and $CO_2$), dimethyl ether, methyl formate, acetone, higher alcohols (ethanol, propanol, butanol), and long-chain hydrocarbons. Commercially, methanol is available in three grades of purity: fuel grade, "A" grade, generally used as a solvent, and "AA" or chemical grade. Chemical grade has the highest purity with a methanol content exceeding 99.85% and is the standard generally observed in the industry for methanol production. The syn-gas generation and purification steps are critical to the existing processes, and the end result would largely depend on the nature and purity of the feedstock. To achieve the desired level of purity, methanol produced by the existing processes is usually purified by sufficient distillation. Another major disadvantage of the existing process for producing methanol through syn-gas is the energy requirement of the first highly endothermic steam reforming step. The process is also inefficient because it involves transformation of methane in an oxidative reaction to CO (and some $CO_2$), which in turn must be reduced to methanol.

Another way to produce syn-gas from methane is through the partial oxidation reaction with insufficient oxygen, which can be performed with or without a catalyst. This reaction is exothermic and is conducted at high temperature of about 1,200° C. to about 1,500° C. The problem with partial oxidation is that the products, CO and $H_2$ are readily further oxidized to form undesired $CO_2$ and water in highly exothermic reactions leading to S values typically well below 2 and contributing to $CO_2$ induced global warming. The following reactions are illustrative of the process.

$$CH_4 + \tfrac{1}{2}O_2 \rightarrow CO + 2H_2 \; \Delta H_{298K} = -8.6 \text{ kcal/mol}$$

$$CO + \tfrac{1}{2}O_2 \rightarrow CO_2 \; \Delta H_{298K} = -67.6 \text{ kcal/mol}$$

To produce syn-gas without either consuming or producing much heat, modern plants are usually combining exothermic partial oxidation with endothermic steam reforming in order to have an overall thermodynamically neutral reaction while obtaining a syn-gas with a composition suited for methanol synthesis (S close to 2). In this process, called autothermal reforming, heat-produced by the exothermic partial oxidation is consumed by the endothermic steam reforming reaction. Partial oxidation and steam reforming can be conducted separately or simultaneously in the same reactor by reacting methane with a mixture of steam and oxygen. The process as mentioned however, produces large amounts of $CO_2$ necessitating its costly sequestering or venting into the atmosphere. Any carbon containing fuel or derived synthetic hydrocarbon product when oxidatively used results in the formation of carbon dioxide and thus is not renewable on the human time scale. There is an essential need to make carbon fuels renewable and thus also environmentally neutral to minimize their harmful effect on global warming.

The selective conversion and recycling of carbon dioxide to methanol without generating unwanted by-products is thus a major challenge and a much desired practical goal. There is a great need to effectively and economically produce methanol from carbon dioxide with high selectivity and yield of conversion.

SUMMARY OF THE INVENTION

The invention now provides novel methods for converting methane and carbon dioxide to methanol without any release of carbon dioxide to the atmosphere or without by-product formation or the use of hydrogen to form water.

In one embodiment, the invention provides for a method of forming methanol, by combining methane, water and carbon dioxide, preferably in a mixture, in single or multiple steps under reaction conditions sufficient to form a molar mixture of hydrogen and carbon monoxide in a specific ratio of at least two moles of hydrogen to one mole of carbon monoxide, and reacting the mixture of hydrogen and carbon monoxide under conditions sufficient to exclusively form methanol. The molar ratio of hydrogen to carbon monoxide is preferably between 2:1 and 2.1:1. The molar ratio between the methane, water and carbon dioxide is about 3:2:1.

In another embodiment, the invention provides for a method of forming methanol by reacting methane and water under steam reforming reaction conditions sufficient to form hydrogen and carbon monoxide, reacting methane and carbon dioxide under dry reforming reaction conditions sufficient to form hydrogen and carbon monoxide, forming a mixture of the combined hydrogen and carbon monoxide in a molar ratio of at least 2 moles of hydrogen to one mole of carbon monoxide, and reacting the carbon monoxide and hydrogen under reaction conditions sufficient to exclusively form methanol. The molar ratio of hydrogen to carbon monoxide is preferably is between 2:1 and 2.1:1. The overall combined molar ratio involving two separate steps between methane, water and carbon dioxide is also about 3:2:1.

In a preferred embodiment, the method comprises:
conducting wet reforming of methane from the methane source with water to form carbon monoxide and hydrogen as follows:

$$2CH_4 + 2H_2O \rightarrow 2CO + 6H_2;$$

conducting dry reforming of methane from the methane source with carbon dioxide to form carbon monoxide and hydrogen as follows:

$$CH_4 + CO_2 \rightarrow 2CO + 2H_2;$$

combining the carbon monoxide and hydrogen from the wet and dry reforming without separation of components to produce a molar mixture of hydrogen and carbon monoxide wherein the hydrogen is present in an amount such that the ratio of hydrogen to carbon monoxide is at least 2:1; and converting molar mixture of hydrogen and carbon monoxide under conditions sufficient to exclusively form methanol, as follows:

$$4CO + 8H_2 \rightarrow 4CH_3OH$$

When the combining of the wet and dry reforming is combined in a single combined bi-reforming step the reactants are provided in a mole ratio of about 3:1:2 as follows:

$$3CH_4 + 2H_2O + CO_2$$

in order to provide the recited molar mixture and ratio of hydrogen and carbon monoxide.

Methanol is foamed over a catalyst on a support at a temperature of from about 800° C. to 1100° C. A preferred catalyst includes a single metal catalyst, a single metal oxide catalyst, a mixed catalyst of a metal and a metal oxide or a mixed catalyst of at least two metal oxides. The catalyst includes V, Ti, Ga, Mg, Cu, Ni, Mo, Bi, Fe, Mn, Co, Nb, Zr, La or Sn or an oxide thereof. The catalyst may be present on a support of a high surface or nano structured oxide, such as fumed alumina or fumed silica. In a specific embodiment, the catalyst is NiO or a mixed catalyst of NiO, $V_2O_5:Ni_2O_3$, $Ni_2V_2O_7$ and $Ni_3V_2O_5$. In a more specific embodiment, the catalyst is NiO supported on fumed alumina or NiO/$V_2O_5$ supported on a fumed silica surface.

BRIEF DESCRIPTION OF THE DRAWING

The features and benefits of the invention will become more evident from review of the following detailed description of illustrative embodiments and the accompanying drawings, wherein:

FIG. 1 shows known examples of methanol-derived chemical products and materials.

DETAILED DESCRIPTION OF THE PREFERRED EMBODIMENTS

The invention relates to processes for the conversion of carbon dioxide from any carbon dioxide source, methane from any methane source such as natural gas, coal bed methane, shale gas, methane hydrate or any other sources to methanol or dimethyl ether. These processes of conversion are referred to as bi-reforming processes and utilize a specific combination of steam ($H_2O$) and dry ($CO_2$) reforming of methane, practiced in two steps or combined into a single step. The method comprises reacting methane or natural gas under a combination of conditions of steam (wet) and dry ($CO_2$) reforming in a specific molar ratio of reactants sufficient to form a mixture of hydrogen/carbon dioxide ($H_2$/CO) in a molar ratio of about 2:1, preferably between 2:1 and 2.1:1, and most preferably about 2.05:1; the ratios that are sufficient to convert such mixture of $H_2$ and CO exclusively to methanol or dimethyl ether. Advantageously, the reactants or mixture of reactants is treated without separation of its components to convert substantially all the reactants to methyl alcohol or, if desired, to dimethyl ether without the production of any by-products. Any unreacted starting or intermediate products can be readily recovered and recycled.

Methanol and dimethyl ether formed by the processes described herein can find utility in numerous applications, either alone, or upon subsequent conversion to other products. Without being limiting, methanol, dimethyl ether and their derived products can be used as synthetic internal combustion engine (ICE) fuels, effective diesel fuels (including mixing varied amounts of dimethyl ether (DME) with conventional diesel fuel), gasoline-methanol mixed fuels (prepared by adding methanol to gasoline with the fuel having a minimum gasoline content of at least 15% by volume). Without being limited as to other uses, methanol and/or dimethyl ether are convenient energy storage and transportation materials in order to minimize or eliminate the disadvantages or dangers inherent in the use and transportation of LNG or LPG. Dimethyl ether is also a convenient household gas to replace natural gas. They are also convenient raw materials for producing olefins (ethylene, propylene etc.) synthetic hydrocarbons, their products and materials, even for preparing single cell proteins for human or animal consumption.

The steps of the process of the invention for the formation of methanol are illustrated by the following reactions:

| Steam Reforming | $2CH_4 + 2H_2O \rightarrow 2CO + 6H_2$ | Step A |
|---|---|---|
| Dry Reforming | $CH_4 + CO_2 \rightarrow 2CO + 2H_2$ | Step B |
| Bi-reforming | $3CH_4 + 2H_2O + CO_2 \rightarrow 4CO + 8H_2$ | Step C |
| | $4CO + 8H_2 \rightarrow 4CH_3OH$ | Step D |

The bi-reforming process of producing methanol can be practiced by carrying out steps A and B separately. The products of reforming of steps A and B are mixed together before being introduced into the methanol producing step D. The steam reforming step is carried by reacting methane and water in an equal molar ratio over a catalyst between 800° C. and 1000° C. The dry reforming step is carried by reacting methane and carbon dioxide in an equal molar ratio over a catalyst between 800° C. and 850° C.

The bi-reforming process of producing methanol can also be practiced by combining the two reforming steps A and B into a single reforming step by reacting methane, water and carbon dioxide in a molar ratio of about 3:2:1 over a catalyst between 800° C. and 1100° C. In many places, natural gas sources also contain substantial amount of $CO_2$.

In one embodiment of the invention, a specific combination of steam and dry reforming of methane is used to achieve a molar ratio of $H_2$ and CO of at least 2 moles hydrogen to 1 mole of carbon monoxide for the conversion to methanol. In another embodiment, methane is treated with water and carbon dioxide in a molar ratio of about 3:2:1 with a temperature range from about 800° C. to about 1100° C., preferably from about 800° C. to about 850° C. To allow conversion, a catalyst or combination of catalysts can be used. These include any suitable metal or metal oxide, including without limitation a metal such as V, Ti, Ga, Mg, Cu, Ni, Mo, Bi, Fe, Mn, Co, Nb, Zr, La or Sn, and corresponding oxides of such metals. The catalysts may be used as a single metal, or a combination of a metal and metal oxide, or a combination of metal oxides, supported on a suitable support such as a high surface area nanostructured oxide support such as fumed silica or fumed alumina. By way of example, NiO, metal-metal oxides such as Ni—$V_2O_5$, ($M_2O_3$—$V_2O_5$), and NiO:$V_2O_5$, as well as mixed oxides such as $Ni_2V_2O_7$ and $Ni_3V_2O_8$ can be used. One of skill in the art would immediately appreciate that a number of other related metal and metal oxide catalysts, and their combinations, can also be used. Suitable reactors for the conversion reactions can also be used. For example, a continuous flow reactor under the appropriate reaction conditions can be used for the reactions to proceed to completion either at ambient pressure or high pressure.

Carbon dioxide is not sequestered or released into the atmosphere and methane is completely converted to methanol without producing any by-product. This provides for significant economical and environmental advantages. By contrast with the processes described herein, the tri-reforming process of methane in which a synergetic combination of dry reforming, steam reforming and partial oxidation of methane is carried out in a single step, but produces by-products ($CO_2$ and $H_2O$) in the oxidation step. By contrast with the tri-reforming process, the process of the invention provides for, control, high selectivity and yield of the conversion of carbon dioxide to methanol without any by-products and without encountering the difficulties and having the disadvantages associated with concurrent partial oxidation resulting in undesirable excess carbon dioxide and water.

The bi-reforming processes of the invention can be used for the preparation of dimethyl ether without water formation as a by-product, as is the case in the presently used dehydration of methanol. This provides an additional advantage as compared to the dry reforming process of producing methane as it gives only a 1:1 molar mixture of CO and $H_2$ and is not suitable without modifications to the production of dimethyl ether as illustrated by the following reaction.

$$CH_4 + CO_2 \rightarrow 2CO + 2H_2$$

For the production of dimethyl ether, water obtained from the dehydration of methanol can be recycled and reacted with carbon dioxide and methane with no by-product ($H_2O$ or $CO_2$) formation in the overall process. Water removal is achieved over a suitable dry silica catalyst or a polymeric perfluoroalkanesulfonic acid catalyst at a temperature of from about 100° C. to 200° C. An example of such catalyst is Nafion-H.

The steps of the process of the invention for the production of dimethyl ether are illustrated by the following reactions:

$$3CH_4 + CO_2 \rightarrow 2CH_3OCH_3$$

$$3CH_4 + 2H_2O + CO_2 \rightarrow 4CO + 8H_2$$

$$4CO + 8H_2 + 4CH_3OH \rightarrow 2CH_3OCH_3 + 2H_2O$$

In an embodiment of the invention, the water formed during the dehydration of methanol is reacted with $CH_4$ and $CO_2$ of about 2:3:1 overall molar ratio to form dimethyl ether. With water recycling, dimethyl ether is formed using methane and $CO_2$ in an overall ratio of about 3:1.

The dry-reforming process of the invention can also be directly applied to natural gas (mixture of hydrocarbons) itself to form methanol or dimethyl ether in a separate step or in a single step with proper selection of mixing to obtain the needed $H_2$ and CO molar mixture of at least 2 moles of hydrogen to one mole of carbon monoxide required for the production of methanol Application to natural gas is illustrated by the following reaction:

$$3C_nH_{(2n+2)} + (3n-1)H_2O + CO_2 \rightarrow (3n+1)CO + (6n+2)H_2 \rightarrow 4nCH_3OH$$

The processes of the invention have significant advantages over the use of syn-gas as it would apply to the production of methanol. Syn-gas of varying compositions can be produced by a variety of reactions. It is generally produced by the reaction of coal, methane, or natural gas with steam (steam reforming). As mentioned in Step B, syn-gas can also be produced by the reaction of $CO_2$ with methane or natural gas in a process called "$CO_2$" or "dry" reforming, because it does not involve steam. The gas mixture produced from methane and $CO_2$, has an $H_2/CO$ ratio close to 1. Therefore, for methanol production, hydrogen generated from other sources must be added to obtain the molar ratio of about 2:1. There is no upper limit for this ratio as long as there is an excess of hydrogen. Therefore, the present invention overcomes this difficulty and produces a $H_2/CO$ mixture with a molar ratio of at least 2 to 1, which is a requirement for the formation of methanol, which is achieved by using a specific combination of steam and dry reforming of methane and substantially all of the hydrogen converted to methanol. As described in U.S. Pat. No. 7,705,059, this subsequent step can be performed, without limitation, by direct catalytic conversion, or by a reaction, which involves methyl formate as an intermediate.

The processes of the present invention allow for the substantially complete utilization of carbon monoxide to form methanol or dimethyl ether. This represents an efficient and economical new way of methanol or dimethyl ether production, as well as an efficient new process for recycling of carbon dioxide into methanol or dimethyl ether, thus rendering the carbon fuels renewable and environmentally carbon neutral. The process is not accompanied by any significant coke formation, as presence of steam in the bi-reforming process retards coke formation and any carbon deposit still formed is in situ converted by reacting with $CO_2$ to form CO.

The processes of the invention to produce dimethyl ether also allow for recycling of the water produced from the subsequent dehydration of formed methanol and do not require the use of external water.

As can be appreciated by one of skill in the art, the energy required for the bi-reforming processes can come from any suitable energy source, including, but not limited to, excess energy fossil burning power plants produced in off peak use periods, any alternative energy sources, atomic energy, etc. The bi-reforming process of methane or natural gas and carbon dioxide to form dimethyl ether is an energy storage and fuel producing process, but not one of energy production.

Natural gas as used in this application would include all conventional natural gas sources, and any suitable source of natural gas or methane can be used. Natural gas is a naturally occurring hydrocarbon gas mixture that primarily includes methane, with up to 20 percent of other hydrocarbons such as ethane as well as small amounts of impurities such as carbon dioxide. Natural gas can be found in deep underground natural rock formations or associated with other hydrocarbon reservoirs, in coal beds, and as methane clathrates. Most natural gas was created over time by two mechanisms: biogenic and thermogenic. Biogenic gas or biogas is created by methanogenic organisms in marshes, bogs, landfills, and shallow sediments. Deeper in the earth, at greater temperatures and pressures, thermogenic gas is created from buried organic material.

Biogas is generally a result of anaerobic bacteria's breaking down organic material in the absence of oxygen. Biogas is produced in the digestive tracks of most mammals, organisms such as termites, and microorganisms during digestion, as well as in wetlands, swamps and bogs, where large amounts of rotting vegetation accumulate. Biogas is composed mainly of methane and carbon dioxide in varying proportions, and contains trace levels of other elements such as hydrogen sulfide ($H_2S$), hydrogen, and/or carbon monoxide.

Shale gas is also a suitable source of methane and other higher hydrocarbons. Shale gas is a conventional natural gas source that is typically obtained after hydraulic fracturing, i.e., the propagation of fractures in a rock layer caused by the presence of a pressurized fluid. Hydraulic fractures may form naturally, as in the case of veins or dikes, or may be man-made in order to release natural gas, coal seam gas, shale gas or other methane containing gases.

Any suitable source of carbon dioxide obtained from any available source can be used, such as, carbon dioxide obtained from emissions of power plants burning fossil fuels, fermentation processes, calcination of limestone, other industrial sources, or even the atmosphere is utilized via its chemical recycling providing renewable carbon fuels into mitigating the environmentally harmful effect of excess $CO_2$. A carbon dioxide source obtained from an exhaust stream from fossil fuel burning power or industrial plant, or a source accompanying natural gas can be used. According to the process of the invention, carbon dioxide is recycled instead of it being sequestered, which provides a way of disposal to the carbon dioxide produced by coal and other fossil fuel burning power plants and industries producing large amounts of carbon dioxide.

The processes of the invention can also utilize carbon dioxide source from the atmosphere. Carbon dioxide content can be separated and absorbed by using various processes as described in U.S. Pat. Nos. 7,378,561 and 7,795,175 or can be recycled chemically as described in U.S. Pat. Nos. 7,605,293 and 7,608,743.

The processes of the invention can also utilize hydrogen derived from a variety of sources, including the electrolysis or cleavage of water. One source of hydrogen can be from the process of steam reforming of natural gas, including, without limitation, in combination with the water gas shift reaction.

The processes of the invention can find multiple applications. Without being limiting, the combination of steam and dry reforming can be used for the recycling of $CO_2$ emissions from coal and other fossil fuels burning power plants. It is also advantageous for use and recycling of $CO_2$ from natural gas sources, which typically contain substantial $CO_2$ concentrations. This is additionally practical, as $CO_2$ would, otherwise, have to be removed to allow further processing of the natural gas. Some natural gas sources contain $CO_2$ concentration from 5 to 20%. For example, the natural gas at the Sleipner platform in Norway contains, for example, 9% $CO_2$. There, the $CO_2$ is currently already separated and sequestered beneath the North Sea in a deep saline aquifer. Other $CO_2$ separation and sequestration processes are already being practiced in Algeria and other locations, but sequestration is only a temporary, costly storage process with the release of large amounts of $CO_2$ when geological events (such as earthquakes) occur.

Another application of the processes of the invention is to the use of methane hydrates. Methane hydrates are composed of methane trapped by water in cage like structures called clathrates. Methane hydrates could be processed using a combination with a bi-reforming process where water in the form of steam is added to react with methane. The transformation to syn-gas and further to methanol or dimethyl ether might render the exploitation of methane hydrates more economical.

EXAMPLES

The following examples illustrate the most preferred embodiments of the invention without limiting it.

Example 1

A suitable molar mixture of $CO_2$, methane (or natural gas) and steam (water) to allow for a conversion of methane and $CO_2$ in excess of 90% is reformed in a single step in a flow reactor over a catalyst such as NiO at a temperature of about 800° C. to 850° C. to produce a gas mixture with a molar ratio of approximately 2.05 moles of hydrogen to one mole of carbon monoxide. In this Example, the catalyst support is fused alumina having a suitably large nanostructured surface. The NiO on fused alumina support is quite stable for the reforming process.

Example 2

A mixture of methane, CO, and $H_2O$ (3:1:2 mole ratio) is reacted over a catalyst composed of $V_2O_5$/NiO supported on nanostructural high surface area fused silica to give a hydrogen/carbon monoxide gas mixture close to 2:1 suitable for the production of methanol.

Example 3

Hydrogen and carbon monoxide produced close to 2:1 ratio, as in Example 1 and 2, are converted to produce methanol under catalytic reaction conditions using copper based catalysts.

Example 4

The methanol produced in Example 3 can be dehydrated to dimethyl ether using a solid acid catalyst such as Nafion H between 100° C. to 200° C.

Example 5

The water formed during the dehydration of methanol to dimethyl ether is reacted with $CH_4$ and $CO_2$ in a 2:3:1 overall molar ratio in the one-step bi-reforming process. With such water recycling dimethyl ether is produced using methane and $CO_2$ in an overall ratio of 3:1.

Example 6

Methane and carbon dioxide in a mole ratio of 1:1 is dry reformed over NiO/$V_2O_5$ on fumed silica at 850° C. in a flow system to obtain a mixture of hydrogen and carbon monoxide in an approximate 1:1 molar ratio.

The invention described and claimed herein is not to be limited in scope by the specific embodiments herein disclosed, as these embodiments are intended as illustrative of several aspects of the invention. Any equivalent embodiments are intended to be within the scope of this invention, as they will become apparent to those skilled in the art from the present description. Such embodiments are also intended to fall within the scope of the appended claims.

What is claimed is:

1. A method of preparing methanol from carbon dioxide, water and a methane source which comprises:
conducting a bi-reforming reaction, wherein the only reactants are methane, carbon dioxide and water in a mole ratio of about 3:1:2 as follows: $3CH_4+2H_2O+CO_2$ by:
conducting wet reforming of methane from the methane source with water to form carbon monoxide and hydrogen as follows:

$$2CH_4+2H_2O \rightarrow 2CO+6H_2;$$

conducting dry reforming of methane from the methane source with carbon dioxide to form carbon monoxide and hydrogen as follows:

$$CH_4+CO_2 \rightarrow 2CO+2H_2;$$

combining effluents consisting of the carbon monoxide and hydrogen from the wet and dry reforming reactions without separation of components of the reforming reactions or their effluents to produce a mixture of hydrogen and carbon monoxide having a molar ratio of hydrogen to carbon monoxide that is 2:1 to 2.1:1; and
converting the molar mixture of hydrogen and carbon monoxide under conditions sufficient to exclusively form methanol, as follows:

$$4CO+8H_2 \rightarrow 4CH_3OH.$$

2. The method of claim 1, wherein the methane, carbon dioxide and water are reacted in the single step.

3. The method of claim 2, wherein the molar mixture of hydrogen and carbon monoxide is present at a mole ratio of 2.05 to 1.

4. The method of claim 2, wherein the combined bi-reforming step is conducted at a temperature of about 800 to 1100° C.

5. The method of claim 2, wherein the bi-reforming is conducted without any significant coke formation.

6. The method of claim 2, wherein the bi-reforming is conducted in the presence of a combination of metal and metal oxide catalysts.

7. The method of claim 6, wherein the catalyst combination is Ni and $V_2O_5$; $Ni_2O_3$ and $V_2O_5$; or $Ni_2V_2O_7$ and $Ni_3V_2O_8$.

8. The method of claim 7, wherein the catalyst combination is supported on a high surface or nanostructured support.

9. The method of claim 8, wherein the support comprises silica, alumina, a metal oxide or a metal.

10. The method of claim 1, wherein the methane source includes any conventional natural gas.

11. A method of preparing methanol from carbon dioxide, water and a methane source which comprises:
conducting a bi-reforming reaction by providing methane, water and carbon dioxide in a mole ratio of 3:1:2 as the only reactants as follows:

$$3CH_4+2H_2O+CO_2;$$

reacting the methane, water and carbon dioxide from the bireforming reaction without separation of the reactants or their effluents to produce an exclusive mixture of hydrogen and carbon monoxide in a mole ratio of 2:1 to 2.1:1; and
reacting the mixture of hydrogen and carbon monoxide under conditions sufficient to exclusively form methanol.

12. The method of claim 11, wherein the reaction of methane, water and carbon dioxide is conducted in a single step.

13. The method of claim 11, wherein the reaction of methane, water and carbon dioxide is conducted by:
wet reforming of methane from the reaction of a methane source with water to form carbon monoxide and hydrogen as follows:

$$2CH_4+2H_2O \rightarrow 2CO+6H_2;$$

dry reforming of methane from a methane source with carbon dioxide to form carbon monoxide and hydrogen as follows:

$$CH_4+CO_2 \rightarrow 2CO+2H_2;$$

and combining effluents of the wet reforming and dry reforming reactions to obtain the mixture of hydrogen and carbon monoxide.

14. The method of claim 12, wherein the molar mixture of hydrogen and carbon monoxide is present at a mole ratio of 2.05 to 1.

15. The method of claim 12, wherein the single bi-reforming step is conducted at a temperature of about 800 to 1100° C.

16. The method of claim 11, wherein the reacting of methane, water and carbon dioxide is conducted without any significant coke formation.

17. The method of claim 11, wherein the reacting of methane, water and carbon dioxide is conducted in the presence of a combination of metal and metal oxide catalysts.

18. The method of claim 17, wherein the catalyst combination is Ni and $V_2O_5$; $Ni_2O_3$ and $V_2O_5$; or $Ni_2V_2O_7$ and $Ni_3V_2O_8$.

19. The method of claim 18, wherein the catalyst combination is supported on a high surface or nanostructured support.

20. The method of claim 19, wherein the support comprises silica, alumina, a metal oxide or a metal.

* * * * *